United States Patent
Engmark et al.

(10) Patent No.: US 6,721,602 B2
(45) Date of Patent: Apr. 13, 2004

(54) IMPLANTABLE MEDICAL DEVICE ASSEMBLY AND MANUFACTURING METHOD

(75) Inventors: David B. Engmark, Bethel, MN (US); Thomas Ceballos, Spring Lake Park, MN (US); Richard A. Bruchmann, Andover, MN (US); Kevin K. Tidemand, East Bethel, MN (US); George Patras, Plymouth, MN (US); Todd Schaefer, Blaine, MN (US); Robert L. Olson, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 140 days.

(21) Appl. No.: 09/934,281

(22) Filed: Aug. 21, 2001

(65) Prior Publication Data

US 2003/0040779 A1 Feb. 27, 2003

(51) Int. Cl.⁷ ............................................... A61N 1/375
(52) U.S. Cl. ........................................................ 607/36
(58) Field of Search ............................. 607/1, 2, 4, 5, 607/9, 36–38

(56) References Cited

U.S. PATENT DOCUMENTS

| | | | | |
|---|---|---|---|---|
| 4,254,775 A | * | 3/1981 | Langer | 607/5 |
| 5,370,669 A | | 12/1994 | Daglow et al. | |
| 5,741,313 A | | 4/1998 | Davis et al. | |
| 6,042,624 A | * | 3/2000 | Breyen et al. | 607/36 |
| 6,157,531 A | | 12/2000 | Breyen et al. | |
| 6,275,369 B1 | | 8/2001 | Stevenson et al. | |

* cited by examiner

Primary Examiner—George R. Evanisko
(74) Attorney, Agent, or Firm—Girma Wolde-Michael; Daniel G. Chapik

(57) ABSTRACT

In general, the invention is directed to an implantable medical device assembly having a more space-efficient housing and components, as well as processes for assembling the implantable medical device with reduced assembly cost and less complexity. The implantable medical device may incorporate a battery, capacitor, circuit assembly, feedthrough assembly, and interconnect assembly with respective electrical terminals. This configuration permits the use of automated electronic module assembly techniques such as parallel gap or ribbon bond welding to electrically connect the terminals. A feedthrough assembly may present a set of terminals adjacent a corresponding set of circuit terminals, also enabling the use of automated welding techniques.

18 Claims, 16 Drawing Sheets

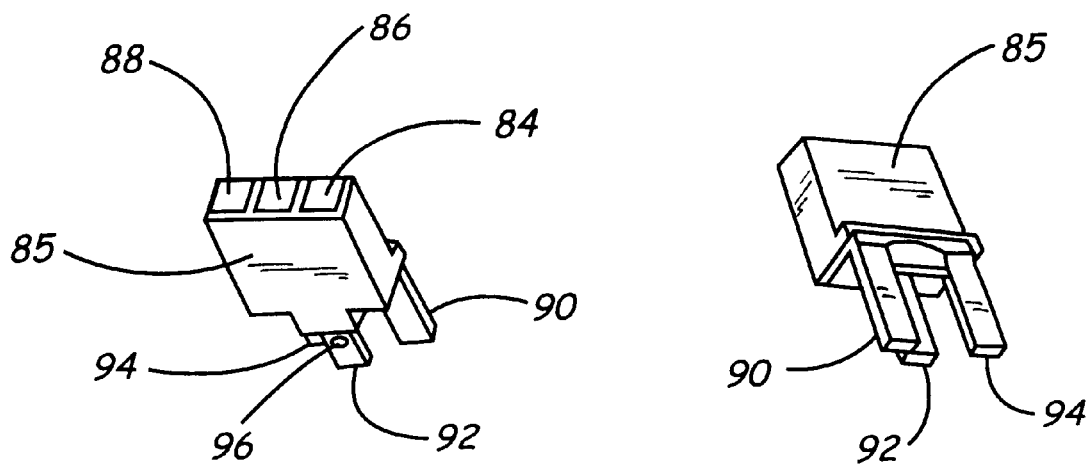
FIG. 18
FIG. 19
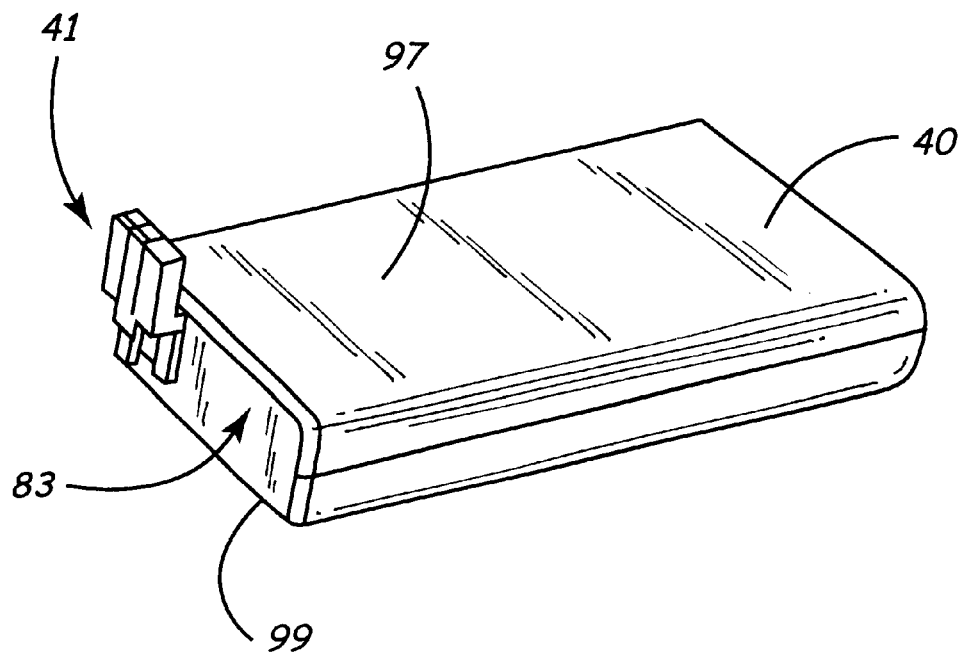
FIG. 20

IMPLANTABLE MEDICAL DEVICE ASSEMBLY AND MANUFACTURING METHOD

FIELD

The invention relates to implantable medical devices and, more particularly, to component assemblies and device assembly processes for manufacture of implantable medical devices.

BACKGROUND

Implantable medical devices typically include a housing that encloses a variety of internal components, and protects them from the implanted environment. Within the human body, for example, the housing must be sealed to prevent the introduction of fluids or moisture. In many cases, however, the implantable medical device includes external components that extend outside of the housing and communicate with the internal components.

One example is an implantable cardioverter/defibrillator (ICD), which includes an internal battery, a charging capacitor, and electronic circuitry. The electronic circuitry ordinarily is coupled to pacing and diagnostic leads that extend outside of the device housing for positioning within or near the heart. To protect internal components while permitting electrical connections with external components, the ICD must include a feedthrough assembly that preserves the environmental integrity of the device housing.

In addition to environmental protection, volume and space efficiency is extremely important in an implantable medical device. In general, it is desirable to make the implantable medical device as small as possible, e.g., for patient comfort and surgical ease. Unfortunately, reduced size can create performance issues. As an example, battery longevity is, in part, a function of battery size. As additional functions are added to an implantable medical device, the size of other internal components can increase. Consequently, space and volume efficiency within the device housing is essential in maintaining performance while permitting incorporation of additional features.

Manufacturability is another concern in the design of implantable medical devices. Many steps in the manufacture and assembly of implantable medical devices still require the careful attention, skill, and time of trained manufacturing personnel. Efforts to simplify or reduce the complexity, cost, and time of the manufacturing and assembly process can directly impact the cost of the implantable medical device for patients. Accordingly, more simple and cost-effective device assembly processes for implantable medical devices are desirable.

SUMMARY

In general, the invention is directed to an implantable medical device assembly having a more space-efficient housing and components, as well as processes for assembly of the implantable medical device with reduced assembly cost and less complexity. In this manner, the invention is capable of promoting overall reductions in the cost of an implantable medical device, while maintaining performance.

The implantable medical device may incorporate a battery, capacitor, circuit assembly, and interconnect assembly with respective electrical terminals arranged in a generally parallel configuration. This configuration permits the use of automated electronic module assembly techniques such as parallel gap or ribbon bond welding to electrically connect the terminals. A feedthrough assembly may present a set of terminals adjacent a corresponding set of additional terminals, also enabling the use of automated welding techniques.

In addition, in some embodiments, the battery and capacitor may be positioned side-by-side, with the circuit assembly sized for placement immediately above the battery. In this case, the combined thickness of the circuit assembly and the battery may be substantially equivalent to the thickness of the capacitor. The interconnect assembly then can be positioned over the circuit assembly and the capacitor. The resulting stacked arrangement is simple to assemble, and provides a reduced thickness profile that promotes space efficiency within the device housing.

In one embodiment, the invention provides an implantable medical device comprising a housing and a battery, capacitor and circuit assembly within the housing. The battery and capacitor have battery terminals and capacitor terminals, respectively, that form a first row of terminals. The circuit assembly has circuit terminals that form a second row of terminals adjacent the first row of terminals. The circuit terminals are electrically coupled to the battery terminals and the capacitor terminals.

In another embodiment, the invention provides a method for assembling an implantable medical device. The method comprises positioning a battery having battery terminals within a housing, positioning a capacitor having capacitor terminals within the housing such that the capacitor terminals form a first row of terminals with the battery terminals, and positioning a circuit assembly having circuit terminals within the housing. The circuit terminals form a second row of terminals. In addition, the circuit assembly is positioned such that the second row of terminals is positioned adjacent the first row of terminals. The method further includes electrically coupling the battery terminals and the capacitor terminals to the circuit terminals using an automated weld process.

In an added embodiment, the invention provides a feedthrough assembly for an implantable medical device. The feedthrough assembly includes an electrically insulative terminal block, and multiple contact elements mounted in an interior side of the insulative terminal block to form feedthrough terminals. First channels formed in an exterior side of the insulative terminal block allow communication of conductive pins to the contact elements. Second channels are formed in the contact elements for receipt of the conductive pins. Multiple electrically conductive pins are threaded through the first and second channels and fixed in place to electrically couple the pins to the contact elements.

In a further embodiment, the invention provides a capacitor assembly for an implantable medical device. The capacitor assembly includes a housing, a capacitor positioned within the housing, and capacitor terminals coupled to respective electrodes of the capacitor. A terminal block assembly carries the capacitor terminals and extends outward from the housing. In particular, the terminal block positions the capacitor terminals for placement adjacent and in substantial linear alignment with battery terminals associated with a battery assembly provided in the implantable medical device.

In an added embodiment, the invention provides a battery assembly for an implantable medical device, the battery assembly comprising a housing, a battery positioned within the housing, battery terminals coupled to respective electrodes of the battery, and a terminal block assembly that carries the battery terminals and extends outward from the housing and positions the battery terminals for placement adjacent and in substantial linear alignment with capacitor terminals associated with a capacitor assembly.

The invention can provide a number of advantages, as mentioned above. For example, the arrangement of the various terminals associated with the battery, capacitor, circuit assembly, and interconnect assembly permits the use of automated part placement and welding techniques to quickly, efficiently, and reliably make the necessary electrical interconnections. With the incorporation of a terminal block assembly, a similar arrangement of terminals can be provided for automated interconnection between the feedthrough assembly and the circuit assembly.

In addition, the stacked configuration of the components and, in particular, the arrangement and size of the circuit assembly relative to the battery and capacitor promotes efficient use of space within the device housing. In this manner, battery size can be preserved despite the incorporation of additional components devoted to enhanced functionality or better performance. Thus, the invention is capable of contributing to overall cost and performance advantages in an implantable medical device.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 18 is a first perspective view of the battery terminal block of FIG. 17.

FIG. 19 is a second perspective view of the battery terminal block of FIG. 17.

FIG. 20 is a perspective view of the battery assembly of FIG. 15.

DETAILED DESCRIPTION

Figure 1:
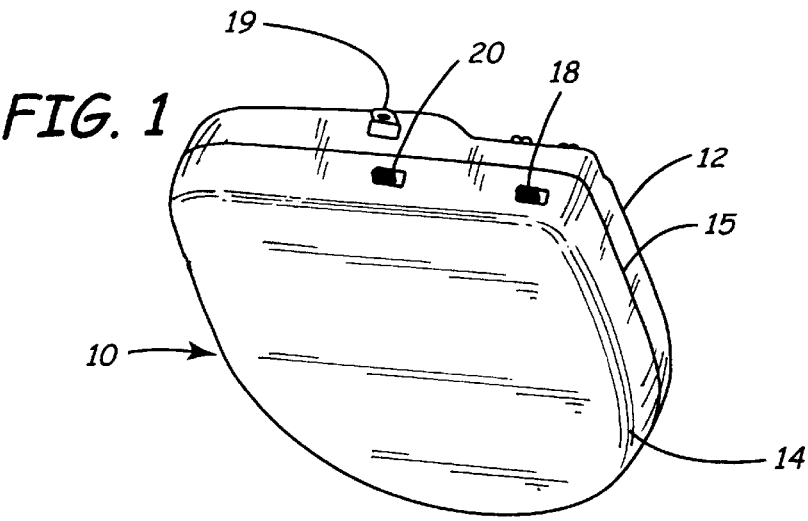
FIG. 1 is a perspective exterior view of an implantable medical device.

FIG. 1 is a perspective view of an implantable medical device 10 in accordance with an embodiment of the invention. In this example, device 10 may take the form of an implantable cardioverter/defibrillator (ICD) for monitoring heart activity and delivering electrical pulses for therapy. The external housing of device 10 includes a first shield 12 and a second shield 14. First and second shields 12, 14 are mounted together to define a seam 15. Seam 15 is welded following placement of the internal components within shields 12, 14 to seal device 10. Together, shields 12, 14 define an enclosure for internal components of device 10. In addition, one or more fasteners 18, 19, 20 may be mounted on the exterior of device 10 for fixation of the device within the implanted environment. Shields 12, 14 and fasteners 18, 19, 20 may be formed from titanium.

Figure 2:
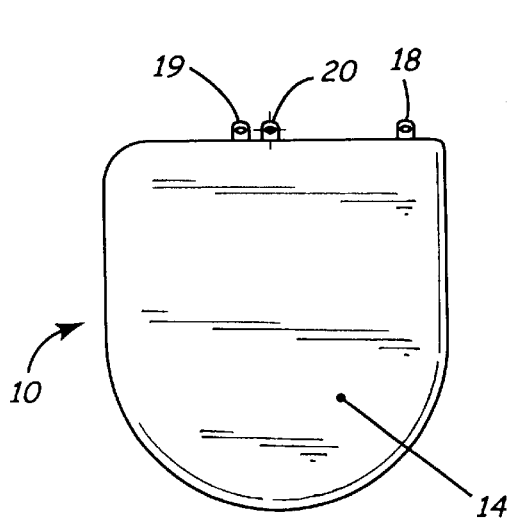
FIG. 2 is a view of a first side of the device of FIG. 1.
Figure 3:
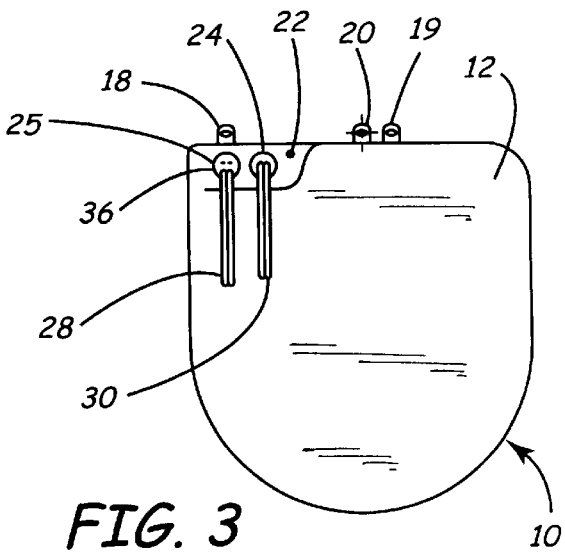
FIG. 3 is a view of a second side of the device of FIG. 1.
Figure 4:
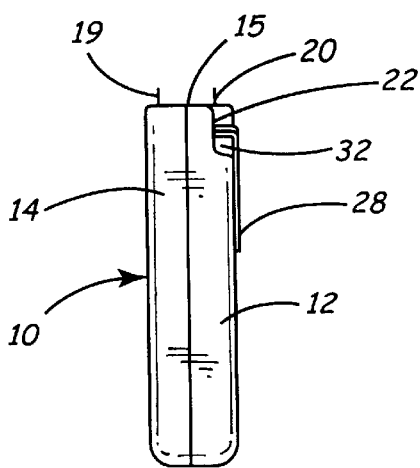
FIG. 4 is an end view of the device of FIG. 1.

FIG. 2 is a view of a first side of the device 10, and illustrates shield 14. FIG. 3 is a view of a second side of device 10, and illustrates first shield 12. FIG. 3 also shows a corner region 22 of first shield 12, in which feedthrough assemblies 24, 26 are mounted. A number of electrically conductive pins 28, 30 extend outward from feedthrough assemblies 24, 26, respectively. The interface between electrically conductive pins 28, 30 and the interior components of device 10 is hermetically sealed to protect the components from the implanted environment. FIG. 4 is an end view of device 10, and illustrates a recessed area 32 that defines corner region 22. As shown, device 10 may have a somewhat curved profile, and is sized for implantation within the human body using conventional techniques.

Figure 5:
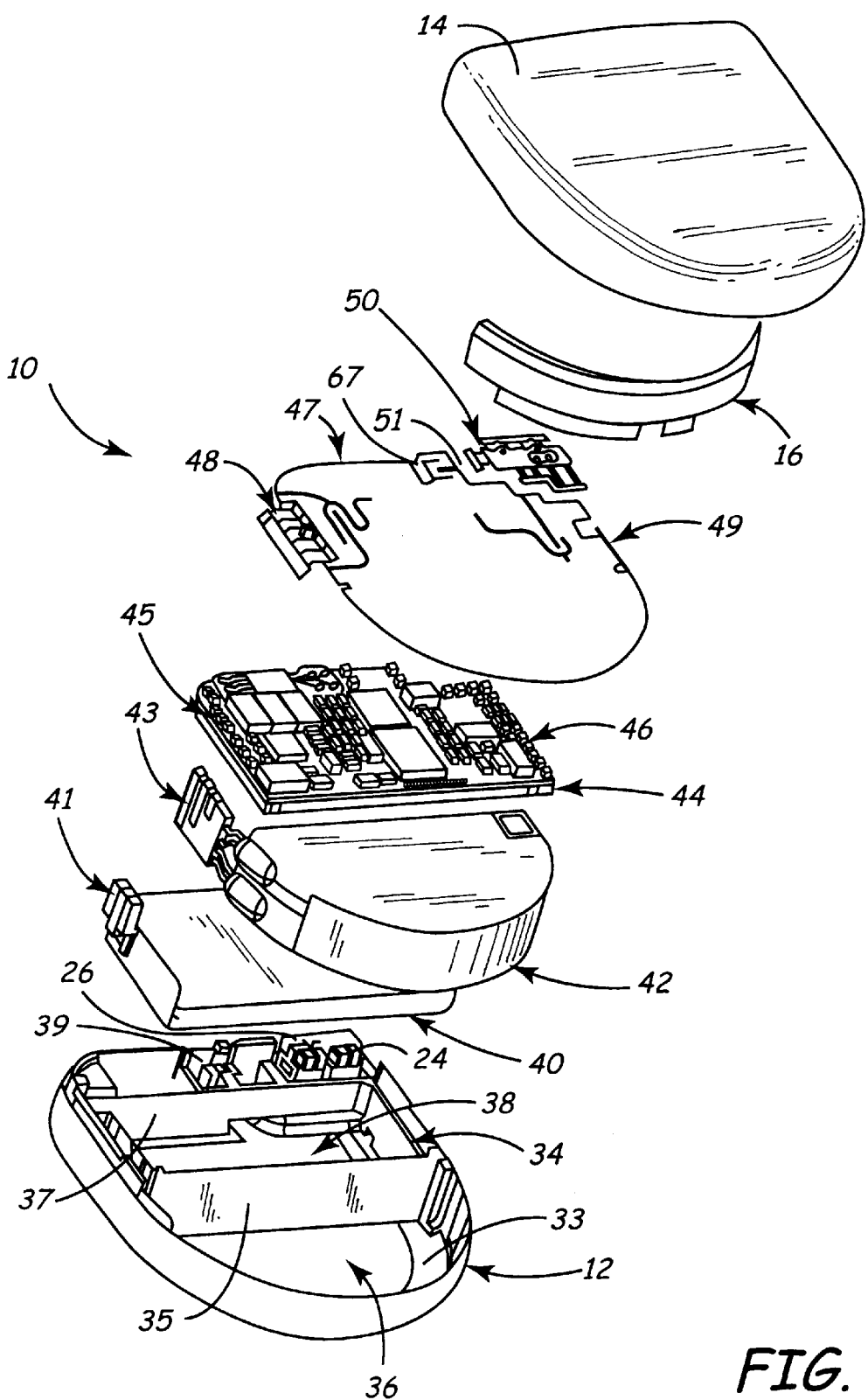
FIG. 5 is an exploded perspective view of the device of FIG. 1.

FIG. 5 is an exploded perspective view of device 10, and illustrates the internal components of the device. In addition to shields 12, 14, device 10 includes an insulative cup 34 and a dessicant 16 mounted within first shield 12. Insulative cup 34 forms walls 35 and 37, which define a first mounting region 36 and a second mounting region 38 disposed side-by-side within first shield 12. Upon assembly, a battery 40 having a battery terminal block 41 is positioned within mounting region 38. Wall 37 segregates mounting region 38 from feedthrough assembly 24, 26, an active can contact 39, and other components mounted within shield 12. A capacitor 42 having a capacitor terminal block 43 is positioned within mounting region 36 adjacent battery 40.

As further shown in FIG. 5, a circuit assembly 44 is positioned over battery 40 and adjacent capacitor 42. Circuit assembly 44 may include a number of terminals, including first and second sets of terminals 45, 46, for electrical interconnection with other components within device 10. As in a conventional ICD, circuit assembly 44 may be equipped with a charging circuit that applies current from battery 40 to charge capacitor 42, and a pulse generation circuit that applies current from the capacitor to deliver electrical pulses to electrical leads associated with feedthrough assemblies 24, 26. Circuit assembly 44 also may include conventional monitoring circuitry for monitoring signals received from leads associated with feedthrough assemblies 24, 26, as well as telemetry circuitry for controlling transmission and reception of radio frequency signals.

Circuit assembly 44 may take the form of a small printed circuit board populated with integrated circuit devices configured to perform the functions of an ICD. An interconnect assembly 47, carrying terminals 48 and 49, is positioned over capacitor 42 and circuit assembly 44. The first set of interconnect terminals 48 are positioned adjacent and electrically coupled to at least some of circuit terminals 45, whereas the second set of interconnect terminals 49 are positioned remotely from circuit terminals 45. Conductors, such as traces within interconnect assembly 47, may electrically couple at least some of the first and second sets of interconnect terminals 48, 49.

Interconnect assembly 47 includes a number of terminals and traces for interconnecting terminals associated with circuit assembly 44 and other components within device 10. Interconnect assembly 47 also may carry a number of electronic components, including an audible alert device and a radio frequency antenna for use in telemetry. Interconnect assembly 47 may take the form of a flex circuit. A smaller flex circuit assembly 50 may be positioned adjacent interconnect assembly 47 and within a cut-out area 51 of the interconnect assembly. Flex circuit assembly 50 includes terminals that are electrically coupled to terminals associated with feedthrough assemblies 24, 26 and circuit assembly 44, as well as interconnection traces.

Upon assembly of battery 40, capacitor 42, circuit assembly 44, and interconnect assembly 47 in a stacked arrangement, and interconnection of the various terminals, shields 12, 14 are coupled together and sealed, e.g., using laser welding techniques. With the stacked arrangement illustrated in FIG. 5, device 10 makes efficient use of interior volume to provide more space for internal components. In addition, as will be apparent, the design of device 10 permits ready use of automated assembly techniques to reduce cost and increased manufacturing speed, particularly in interconnecting the terminals of the various components.

Figure 6:
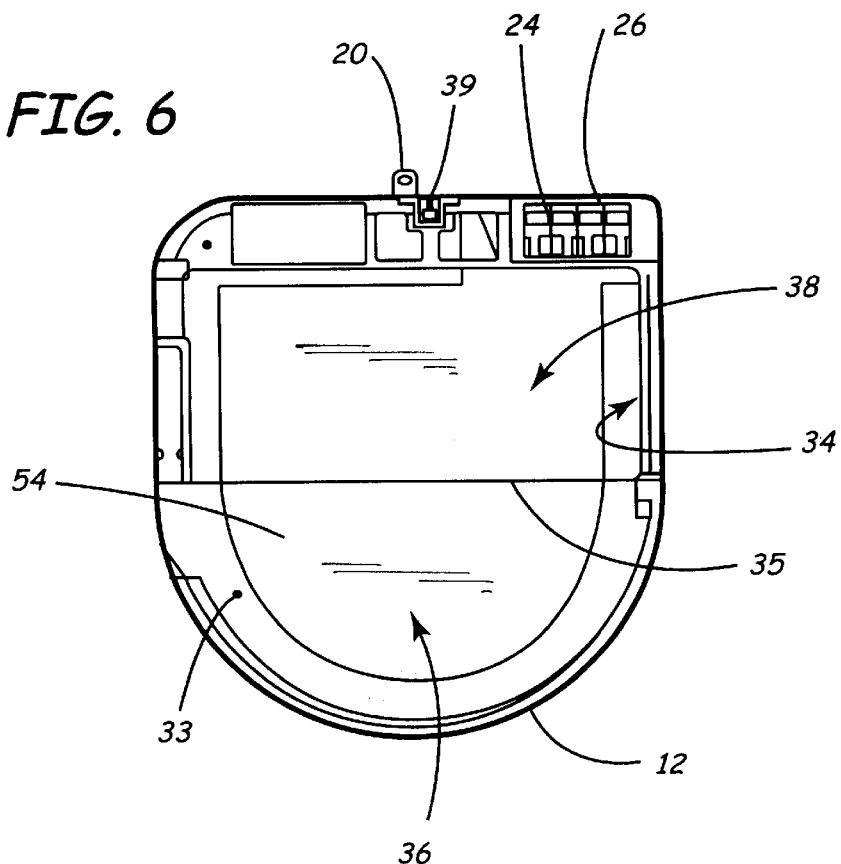
FIG. 6 is an interior view of one side of a housing associated with the device of FIG. 1 at a first stage in an assembly process.

FIG. 6 is an interior view of one side of a housing associated with device 10, i.e., shield 12, at a first stage in an assembly process. As shown in FIG. 6, insulative cup 34 defines mounting regions 38 and 36 for battery 40 and capacitor 42. In addition, a generally U-shaped insulative liner 33 is positioned within the interior surface 54 of shield 12, and serves as an insulative support for battery 40 and capacitor 42. In particular, insulative liner 33 insulates battery 40 and capacitor 42 from shield 12. Insulative cup 34 may be automatically positioned within shield 12 using automated assembly techniques.

Figure 7:
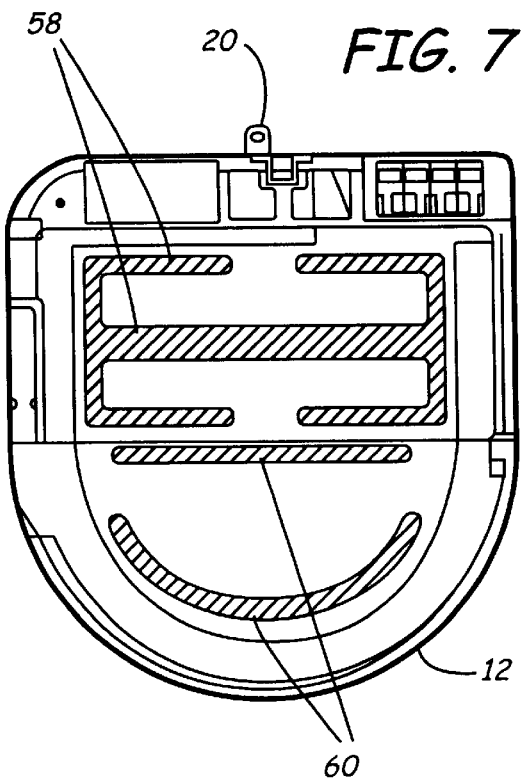
FIG. 7 is an interior view of the housing of FIG. 6 at a second stage in the assembly process showing application of adhesive material.

FIG. 7 is an interior view of device 10 at a second stage in the assembly process showing application of an adhesive material 58, 60 to the bottom interior surface 54 of shield 12 within mounting regions 38, 36, respectively. Adhesive material 58, 60 may take the form of a conventional epoxy resin and a catalyst that are automatically applied to the interior surface of shield 12 just prior to placement of battery 40 and capacitor 42.

Figure 8:
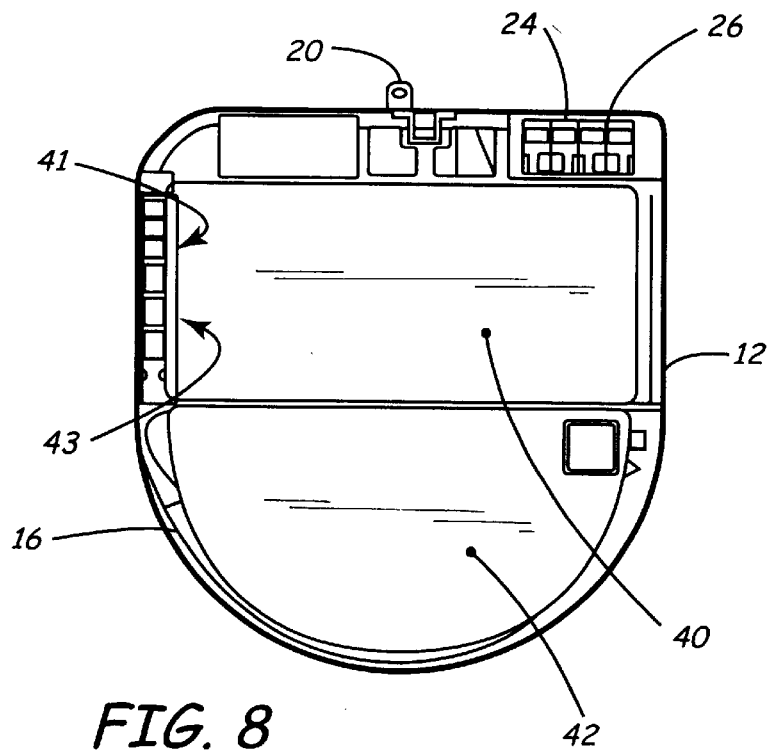
FIG. 8 is an interior view of the housing of FIG. 6 at a third stage in the assembly process showing placement of a battery and capacitor.

As shown in FIG. 8, at a third stage in the assembly process, battery 40 and capacitor 42 are placed within mounting regions 38, 36, respectively. Again, battery 40 and capacitor 42 can be automatically positioned within insulative cup 34, which provides a guide for placement within regions 36, 38. FIG. 8 also shows the arrangement of battery terminal block 41 and capacitor terminal block 43 adjacent one another. In the example of FIG. 8, the terminals in battery terminal block 41 and capacitor terminal block 43 are in generally linear alignment and form a first row of terminals. As will be described, capacitor terminal block 43 extends away from capacitor 42 for placement immediately adjacent battery terminal block 41.

Adhesive material 58, 60 bonds battery 40 and capacitor 42 to interior surface 54 of shield 12. Insulative liner 33 serves to isolate battery 40 and capacitor 42 from the interior surface 54. Insulative cup 34 isolates battery 40 and capacitor 42 from one another and serves to align the battery and capacitor within mounting regions 38, 36 for subsequent assembly stages. In addition, battery 40 and capacitor 42 may include outer insulative layers that prevent electrical contact with shield 12. Battery 40 and capacitor 42 preferably conform in size and shape to mounting regions 38, 36, respectively, and thereby fill substantially all of the space within those regions. Battery 40 has a thickness, however, that is significantly less than the thickness of capacitor 42. The difference in thickness permits circuit assembly 44 to be mounted above battery 40 within mounting region 38.

Figure 9:
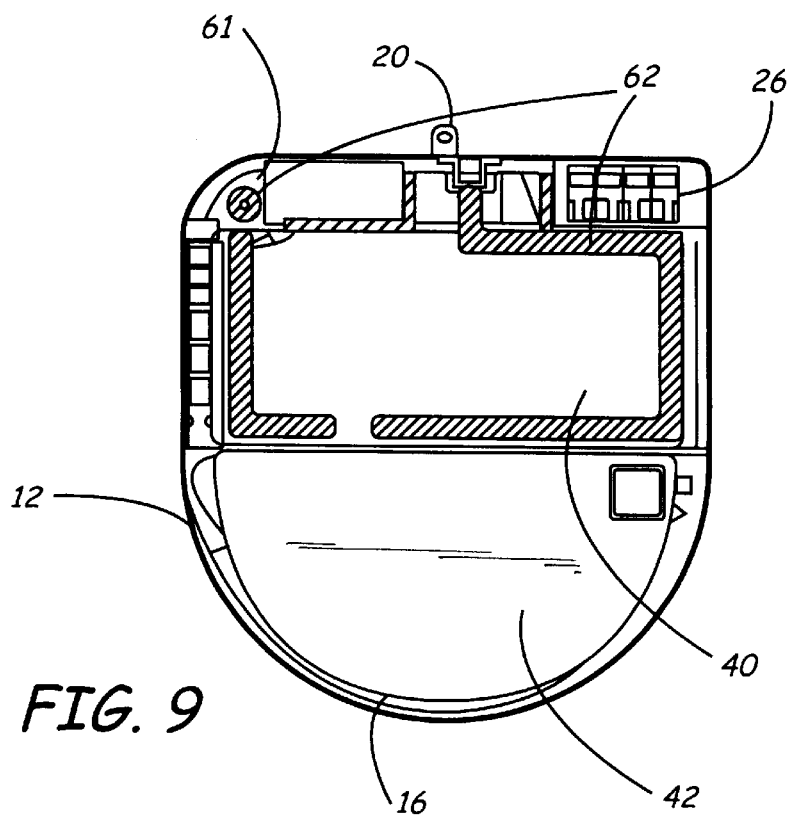
FIG. 9 is an interior view of the housing of FIG. 6 at a fourth stage in the assembly process showing application of an adhesive material to the battery.

FIG. 9 shows the interior of shield 12 in a fourth stage in the assembly process in which adhesive material 62 is applied to an upper surface of battery 40 and to a raised area 61 that forms part of insulative cup 34 within shield 12. Again, adhesive material 62 may take the form of an epoxy resin and catalyst selected to effectively bond circuit assembly 44 to battery 40.

Figure 10:
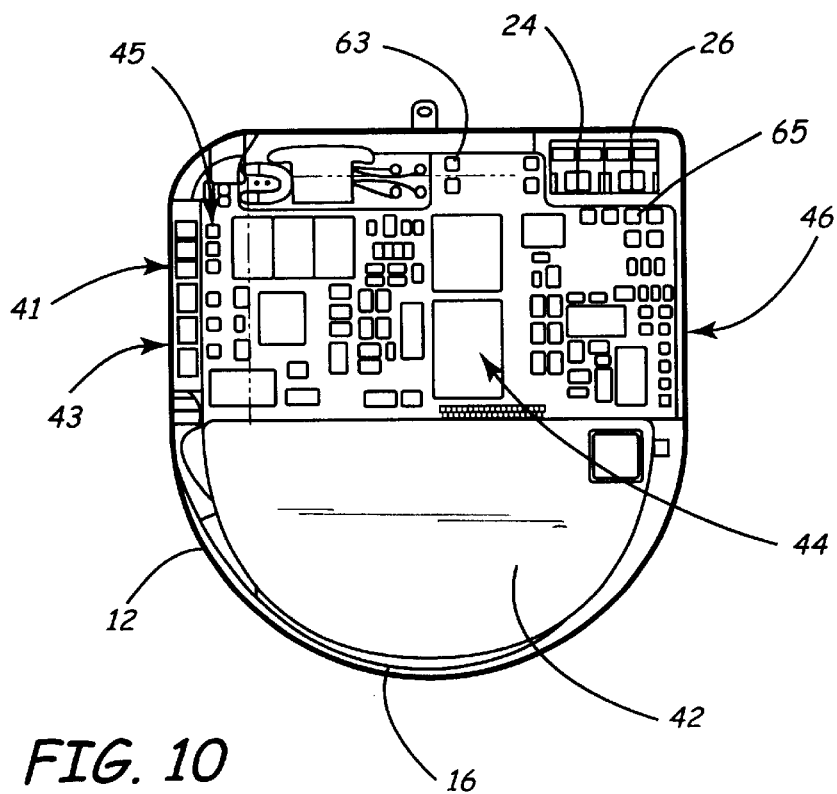
FIG. 10 is an interior view of the housing of FIG. 6 at a fifth stage in the assembly process showing placement of a circuit assembly over the battery.

FIG. 10 shows fifth stage in the assembly process in which circuit assembly 44 is positioned over battery 40 and bonded to the battery via adhesive material 62. As shown in FIG. 10, circuit assembly 44 occupies substantially all of the surface area above battery 40 with the exception of the area above terminal blocks 41, 43 and feedthrough assemblies 24, 26.

Circuit assembly 44 may be positioned automatically, and makes efficient use of the interior space within shield 12. In particular, the combined thickness of battery 40 and circuit assembly approximates the thickness of capacitor 42. In this manner, the stacked arrangement of battery 40 and circuit assembly 44, in combination with the adjacent capacitor 44, presents a generally planar upper surface. Thus, battery 40, capacitor 42, and circuit assembly 44 consume substantially all of the volume afforded by insulative cup 34, resulting in efficient use of space within device 10.

Circuit assembly 44 includes a first set of terminals 45 on one edge and a second set of terminals 46 on another edge. Terminals 45, 46 may take the form of conductive pads or bumps formed on the circuit board substrate of circuit assembly 44. Circuit assembly 44 may include additional terminals 63, 65 positioned proximate active can contact 39 and feedthrough assemblies 24, 26, respectively. Notably, the terminals in each set 45, 46 are in linear alignment and form a row of terminals. As shown in FIG. 10, the placement of circuit assembly 44 over battery 40 serves to position the first set of circuit terminals 45 adjacent the battery and capacitor terminal blocks 41, 43. In particular, circuit terminals 45 form a second row of terminals that extends generally parallel to the first row of terminals formed by terminals 41, 43.

In addition, the individual terminals in each row preferably are positioned immediately across from a corresponding terminal in the other row. Specifically, opposing terminals in each row preferably are intended to be electrically coupled to one another across the small gap between the first and second rows of terminals. In this manner, electrical connections can be readily made between terminals 41, 43 and terminals 45 using automated techniques such as parallel gap or ribbon bond welding. In addition, automated pick-and-place techniques can be used to position and fix battery 40, capacitor 42, and circuit assembly 44 within shield 12 and position the terminal blocks 41, 43 and terminals 45 adjacent one another.

Figure 11:
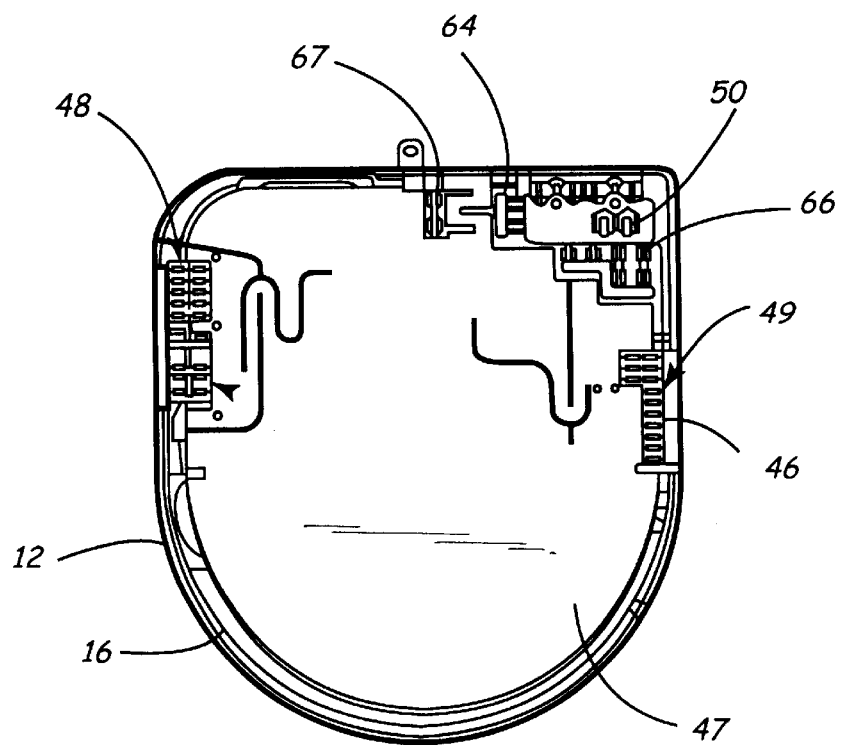
FIG. 11 is an interior view of the housing of FIG. 6 at a sixth stage in the assembly process showing placement of an interconnect assembly over the circuit assembly and capacitor.

The interconnections between battery 40, capacitor 42 and circuit assembly 44 are facilitated by incorporation of interconnect assembly 47. FIG. 11 shows a sixth stage in the assembly process in which interconnect assembly 47 is placed over circuit assembly 44 and capacitor 42. Interconnect assembly 47 may be fixed within shield 12 using, for example, a pressure sensitive adhesive that bonds a bottom side of the interconnect assembly to the generally planar upper surface provided by capacitor 42. The pressure sensitive adhesive can be applied directly to the lower surface of interconnect assembly 47, e.g., on alert device 78 shown in FIG. 13, and covered with a release liner for removal prior to assembly. Interconnect terminals 48 align over battery terminals 41, capacitor terminals 43, and circuit terminals 45. In addition, interconnect terminals 49 align over circuit terminals 46. Interconnect assembly 47 may include other terminals 67 that align over terminals 63 of circuit assembly 44. Dessicant 16 may be added to shield 12 prior to welding shields 12 and 14 together.

Figure 12:
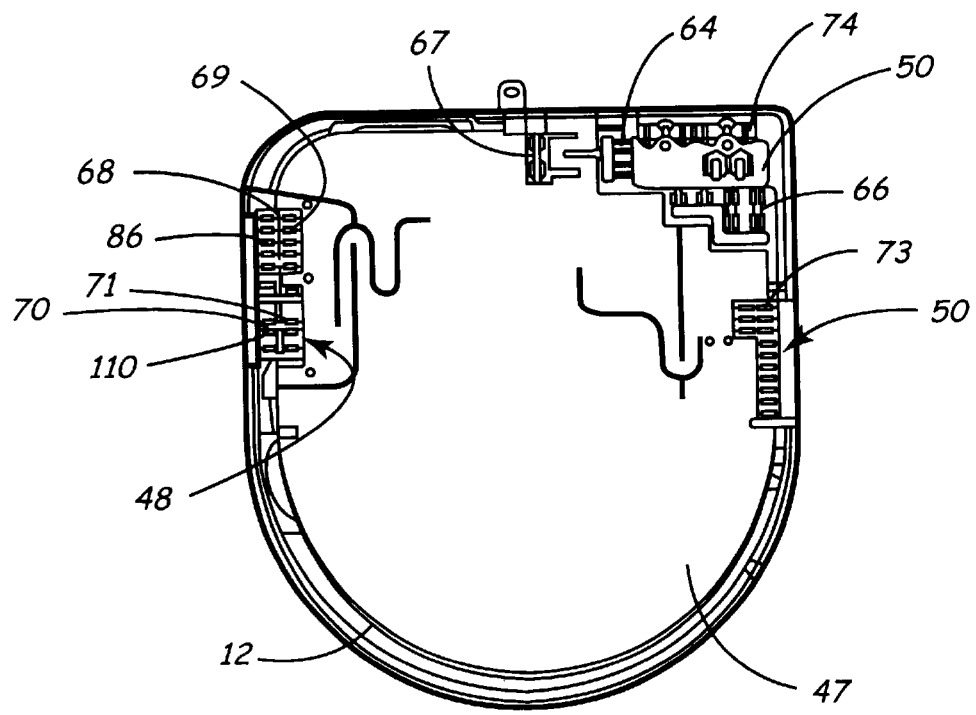
FIG. 12 is an enlarged view of the assembly of FIG. 11.

FIG. 12 is an enlarged view of the assembly of FIG. 11. As shown in FIG. 12, interconnect assembly 47 may include a number of interconnect terminals in the form of conductive ribbons 68. Conductive ribbons 68 bridge the gaps between terminals in battery terminal block 41 and adjacent terminals in circuit assembly 44, as well as the gaps between terminals in capacitor terminal block 43 and adjacent terminals in the circuit assembly 44. As an example, a conductive ribbon 68 bridges the gap between a circuit terminal 69 on circuit assembly 44 and a battery terminal 86 on battery terminal block 41. Similarly, a conductive ribbon 70 bridges the gap between a circuit terminal 71 on circuit assembly 44 and a capacitor terminal 110 on capacitor terminal block 43. Conductive ribbon 70 is parallel gap welded by an automated welding device to fuse it to terminals 71, 110 and form an electrical connection. In this manner, the first and second rows of terminals provided by terminal block 41, 43 and terminals 45, respectively, are electrically coupled to one another. As an alternative to parallel gap welded bonds, other automated welding techniques such as ribbon bond welding could be used to interconnect the various terminals.

Upon registration of interconnect assembly 47 over circuit assembly 44 and capacitor 42, the various terminals and conductive ribbons 68 readily align with one another. Thus, an automated welding device can be used to quickly fuse the conductive ribbons to the opposing terminals, and thereby create welded electrical interconnections between battery 40, capacitor 42, circuit assembly 44 and interconnect assembly 47. Similar interconnections can be provided at other points between interconnect assembly 47 and circuit assembly 44, as indicated, for example, by reference numerals 73, 67. In addition, flex circuit 50 provides interconnections between terminals associated with feedthrough assemblies 24, 26 and circuit terminals on circuit assembly 44, as indicated by reference numerals 64, 66, 74. In this manner, circuit assembly 44 can then provide interconnections, via conductive traces, between circuit terminals on circuit assembly 44 and the feedthrough terminals. The ready alignment of the various terminals adjacent one another and, consequently, the availability of automated welding techniques, greatly simplifies the assembly process for device 10.

Figure 13:
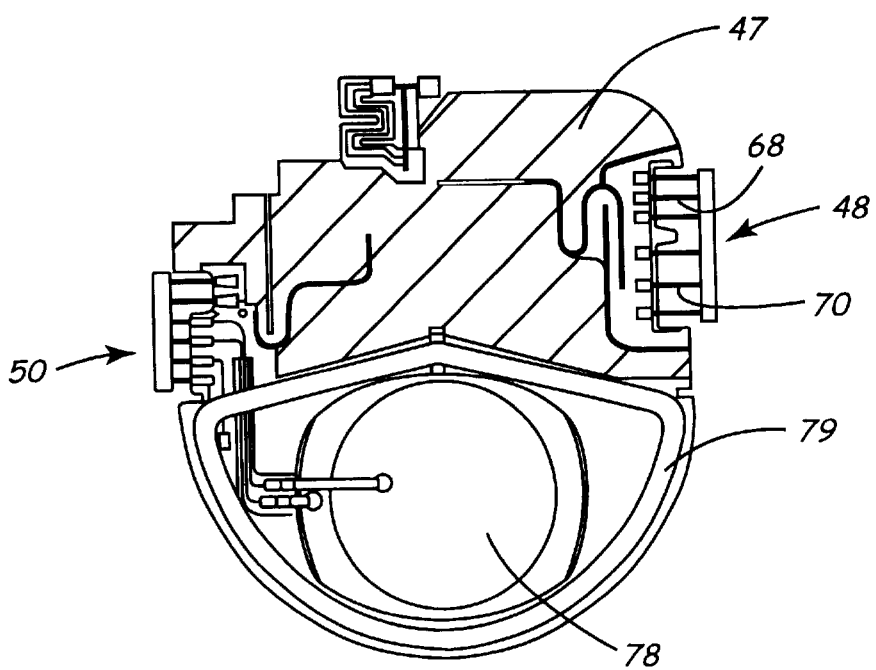
FIG. 13 is a view of an opposite side of the interconnect assembly shown in FIG. 11.

FIG. 13 is a view of an opposite side of interconnect assembly 47. As shown in FIG. 13, interconnect assembly 47 may include an audible alert device 78 and a radio frequency antenna 79. Alert device 78, which may take the form of a piezoelectric element, and antenna 79 may be electrically coupled to at least some of the terminals in circuit assembly 44 via terminals in interconnect assembly 47. Interconnect assembly 47 also may include circuit traces that electrically couple various interconnect terminals with one another, and thereby interconnect circuit assembly 44 to components on the interconnect assembly, and battery 40 and capacitor 42 to the circuit assembly. Shield 14 is mounted relative to shield 12 to enclose the resulting stack of components. Advantageously, each of the components can be placed within shield 12 from the same direction in a stacked arrangement, facilitating the use of automated pick-and-place devices.

Figure 14:
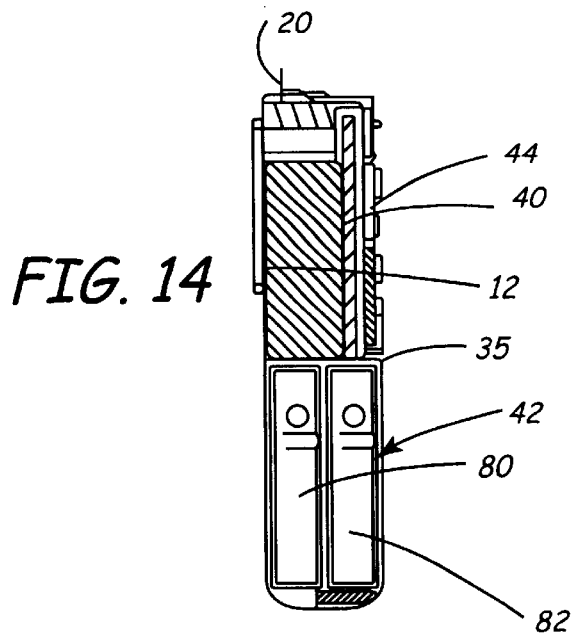
FIG. 14 is a cross-sectional side view of the assembly of FIG. 10 in the fifth stage of the assembly process.

FIG. 14 is a cross-sectional side view of the assembly of FIG. 10 in the fifth stage of the assembly process, i.e., prior to addition of interconnect assembly 47. As shown in FIG. 14, capacitor 42 can be formed by a pair of capacitor elements 80, 82 integrated with one another in a common package. Capacitor elements 80, 82 may be electrically coupled in series. FIG. 14 also illustrates the stacked arrangement and thickness dimensions of battery 40, capacitor 42, and circuit assembly 44. For example, when stacked together, battery 40 and circuit assembly 44 may have a combined thickness that approximates the thickness of capacitor 42, making efficient use of available space. In addition, circuit assembly 44 and capacitor 42 present a generally planar surface for positioning of interconnect assembly 47.

Figure 15:
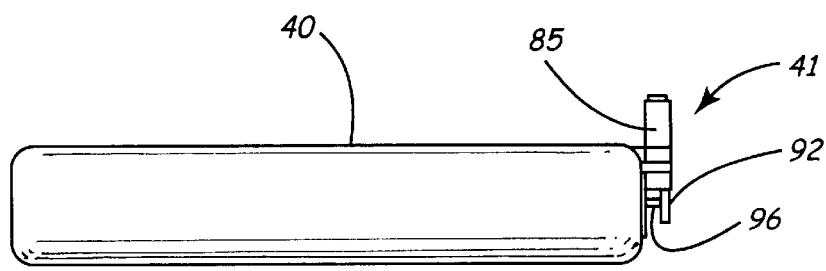
FIG. 15 is a side view of a battery assembly.
Figure 16:
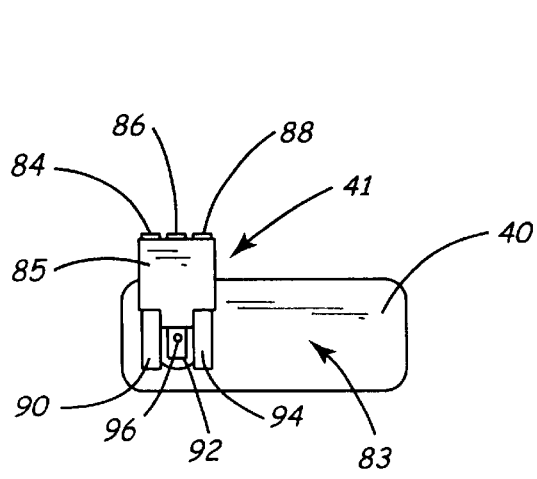
FIG. 16 is an end view of the battery assembly of FIG. 15.
Figure 17:
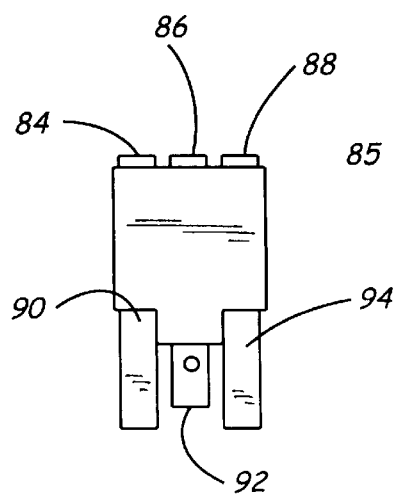
FIG. 17 is a front view of a battery terminal block associated with the battery assembly of FIG. 15.

FIG. 15 is a side view of a battery 40 for use in device 10. As shown in FIG. 15, battery 40 may be generally rectangular in shape, and includes a battery terminal block 41 along a side surface 83 of the battery housing. FIG. 16 is an end view of battery 40, illustrating battery terminal block 41 in greater detail. FIG. 17 is a front view of battery terminal block 41. FIGS. 18 and 19 are perspective views of battery terminal block 41. FIG. 20 is a perspective view of battery 40.

As illustrated in FIGS. 15–20, battery terminal block 41 includes a terminal block body 85, and conductive battery terminals 84, 86, 88. Battery terminals 84, 86, 88 may extend through block body 85, and form terminal leads 90, 92, 94 that are mounted to battery 40. Battery terminals 84, 86, 88 and corresponding leads 90, 92, 94 may be insert-molded in terminal block body 85, which can be formed from a plastic material such as liquid crystal polymer (LCP). Notably, battery terminals 84, 86, 88 and each corresponding lead 90, 92, 94 may be integrally formed with one another. In particular, leads 90, 92, 94 may extend through terminal block body 85 to form terminals 84, 86, 88, respectively.

Terminal leads 90, 92, 94 may contact terminals from battery 40 and correspond to battery negative, positive, and negative terminals, respectively, within the battery. In particular, leads 90, 94 can be welded to battery surface 83, which forms a negative electrode, whereas lead 92 can be welded to a feedthrough terminal 96 that extends outward from battery 40 and forms a positive electrode. This arrangement provides for easy attachment of battery terminal block 41 to battery 40 and yields a strong and reliable attachment. In addition, the structure of battery terminal block 41 promotes the use of automated device assembly and welding techniques.

With reference to FIG. 20, insulating layers 97, 99 can be added to the top and bottom surfaces, respectively, of battery 40 to isolate the battery from shield 12 and circuit assembly 44. Opposite ends of top insulating layer 97 can be tucked inside of the ends of bottom insulating layer 99 to prevent the insulator from catching on the walls of insulative cup 34 upon insertion into shield 12 during assembly.

Figure 21:
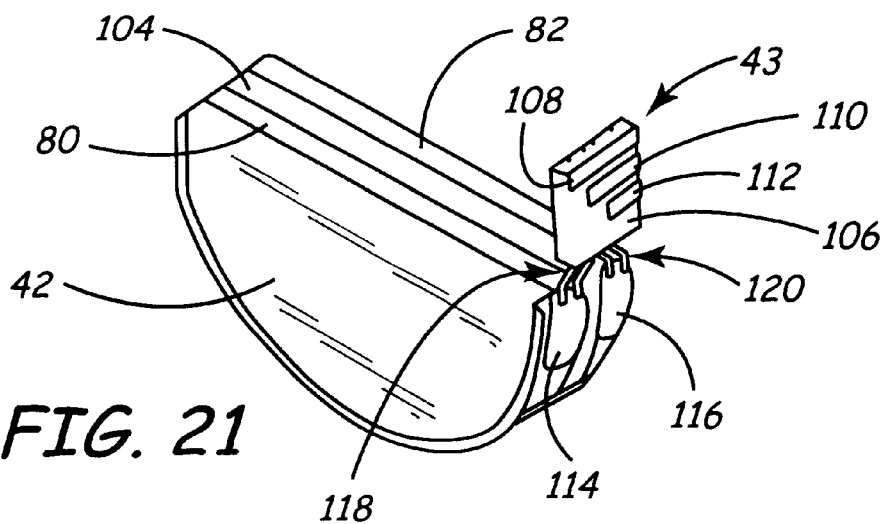
FIG. 21 is a perspective view of a capacitor assembly.
Figure 22:
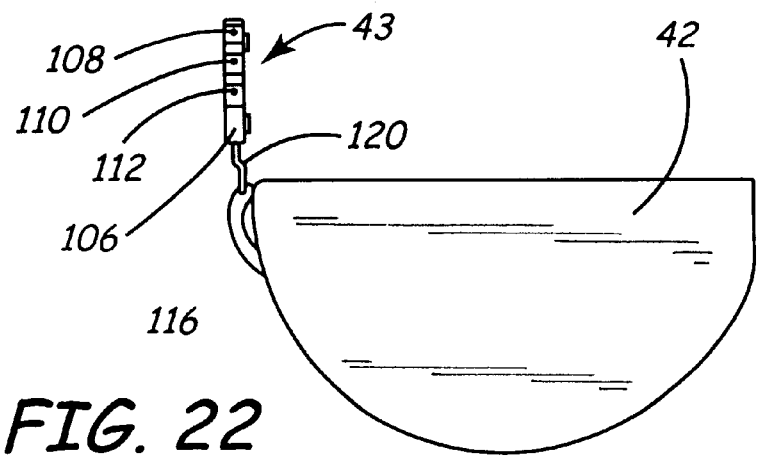
FIG. 22 is a plan view of the capacitor assembly of FIG. 21.
Figure 23:
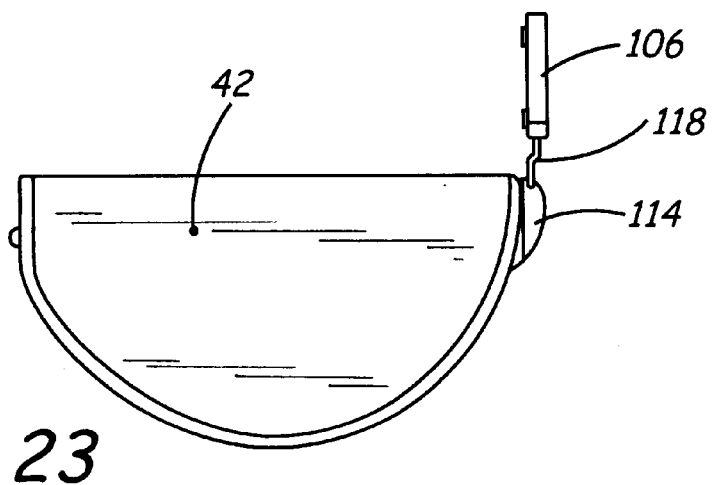
FIG. 23 is a plan view of the capacitor assembly of FIG. 21 taken from a side opposite that shown in FIG. 22.
Figure 24:
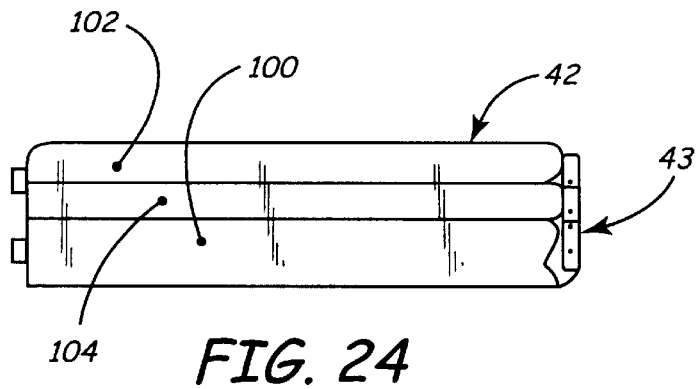
FIG. 24 is a side view of the capacitor assembly of FIG. 21.
Figure 25:
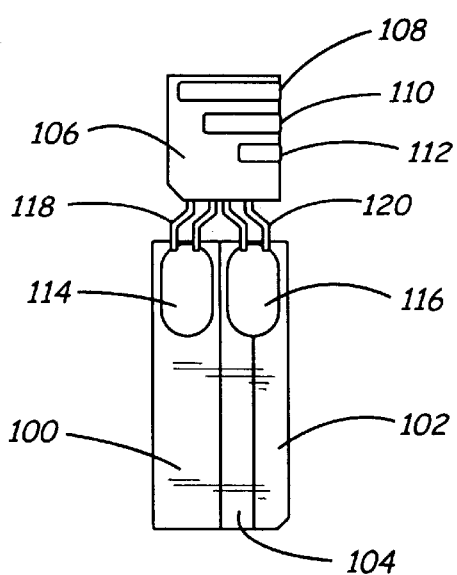
FIG. 25 is an end view of the capacitor assembly of FIG. 21.

FIG. 21 is a perspective view of capacitor 42. FIGS. 22 and 23 are opposite plan views of capacitor 42, whereas FIGS. 24 and 25 are side and end views, respectively. As shown, capacitor 42 is somewhat hemispherical in shape to more effectively conform to the inner curvature of shield 12. Capacitor 42 includes capacitor elements 80, 82 and an intermediate insulator 104. In addition, capacitor 42 includes capacitor terminal block 43 with a capacitor terminal block body 106 and capacitor terminals 108, 110, 112. Capacitor terminal block body 106 may be formed from a plastic material, such as liquid crystal polymer. Capacitor terminals 108, 110, 112 are coupled to capacitor 42 via conductor pairs 118, 120 which extend outward from mounting points 114, 116.

Each pair of conductors 118, 120 has one conductor that is electrically coupled to a positive electrode and one conductor coupled to a common electrode of a respective capacitor element 80, 82. Capacitor elements 80, 82 may be connected in series. Capacitor terminals 108, 110, 112 are coupled to conductor pairs 118, 120 such that terminal 108 is coupled to the positive electrode of capacitor element 80, terminal 112 is coupled to the positive electrode of capacitor element 82, and terminal 110 is coupled to the common electrodes of both capacitor elements. Capacitor terminals 108, 110, 112 may be insert-molded within capacitor block body 106.

Figure 26:
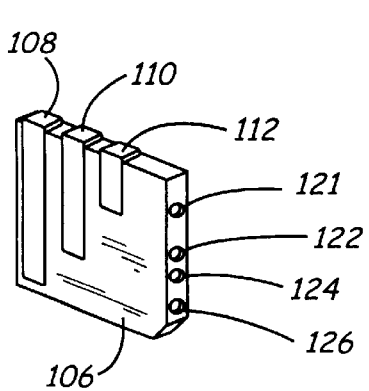
FIG. 26 is a first perspective view of a terminal block associated with the capacitor assembly of FIG. 21.
Figure 27:
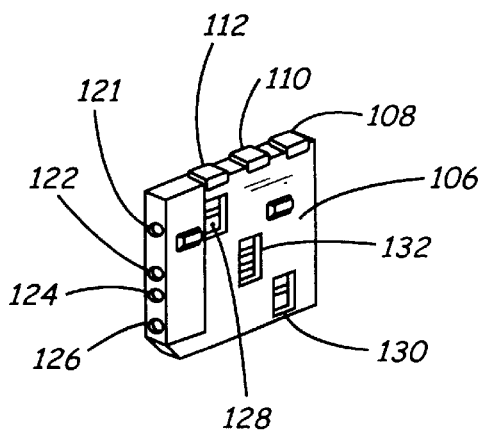
FIG. 27 is second perspective view of a terminal block associated with the capacitor assembly of FIG. 21.

FIGS. 26 and 27 are first and second perspective views of capacitor terminal block 43. As shown, terminal block body 106 includes a number of channels 121, 122, 124, 126 that communicate with terminals 108, 110, and 112. Channels 121, 122, 124, 126 receive individual conductors of conductor pairs 118, 120. Channels 121 and 126 receive conductors coupled to the positive electrodes of capacitor elements 80, 82 for interconnection with terminals 112 and 108, respectively. Channels 122 and 124 receive the conductors coupled to the common electrodes for interconnection with terminal 110. Channels 121 and 126 terminate at apertures 128, 130, respectively, which permit the positive electrode conductors to be welded to terminals 112 and 108. Channels 122, 124 terminate at aperture 132, permitting the common electrode conductors to be welded to terminal 110. In particular, the conductors can be threaded through channels 121, 122, 124, 126 and welded in place, permitting easy attachment and promoting attachment reliability and strength.

In addition to carrying electrical conductors, conductor pairs 118, 120 serve to form a terminal block arm that extends capacitor terminal block 43 outward from capacitor 42 for placement adjacent battery terminal block 41. In particular, capacitor terminal block 43 positions the capacitor terminals adjacent the battery terminals and generally parallel to a lateral surface 83 of battery 40 in substantial alignment to form the first row of terminals. For this reason, conductor pairs 118, 120 may be sheathed in a semi-rigid material sufficient to support terminal block 43 to some degree, although a platform may be provided within insulative cup 34 to support terminal blocks 41, 43.

As capacitor 42 is placed within mounting region 36, capacitor terminal block 43 is placed in alignment with battery terminal block 41 to form a first row of terminals. Thus, capacitor terminal block 43 extends outside of mounting region 36. Upon placement of circuit assembly 44 over battery 40, circuit terminals 45 form a second row of terminals adjacent battery terminal block 41 and capacitor terminal block 43. Thus, the arrangement of battery terminal block 41 and capacitor terminal block 43 relative to circuit terminals 45 promotes automated assembly and automated interconnect welding.

Figure 28:
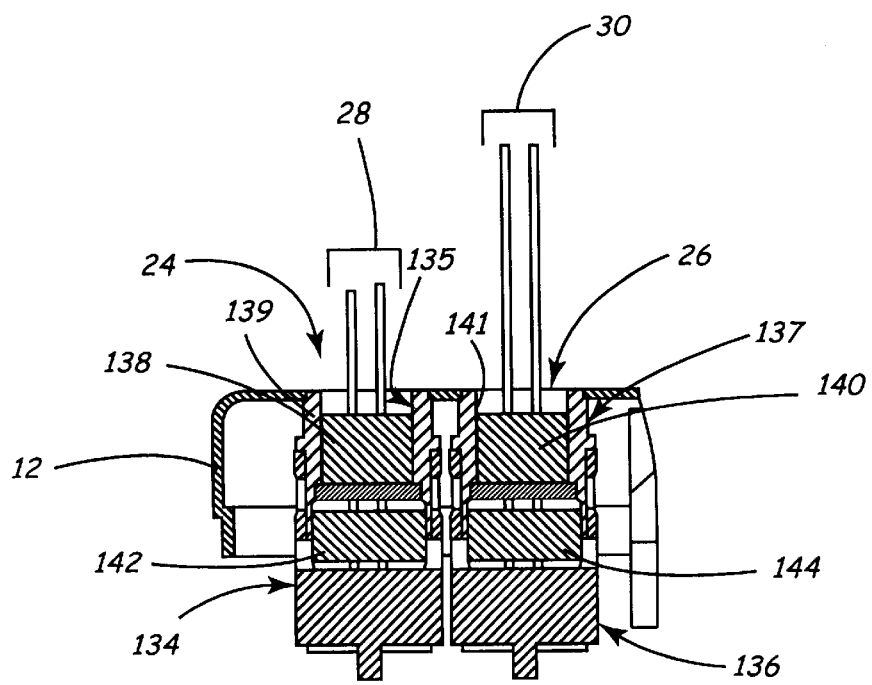
FIG. 28 is a cross-sectional view of a pair of feedthrough assemblies.
Figure 29:
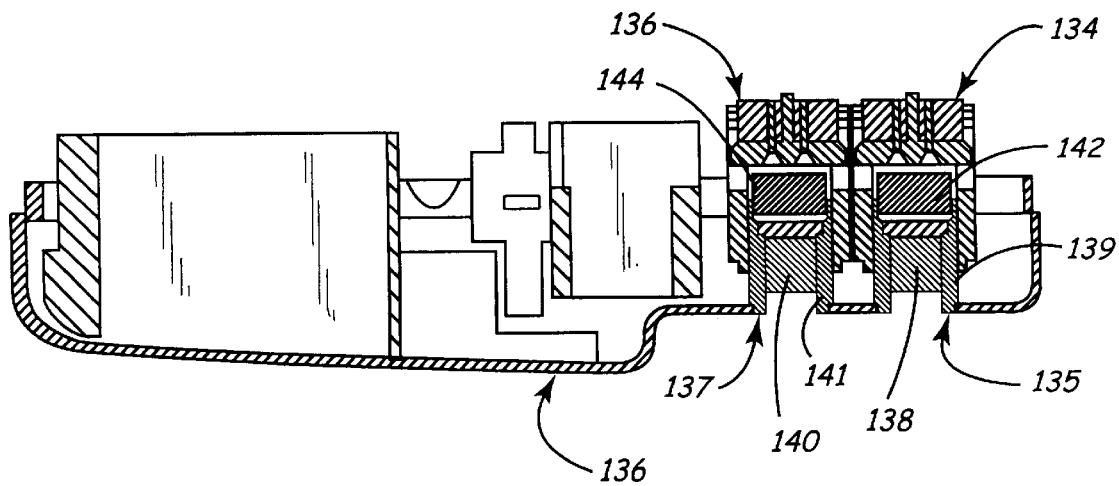
FIG. 29 is another cross-sectional view of feedthrough assemblies in conjunction with a portion of the device housing.
Figure 30:
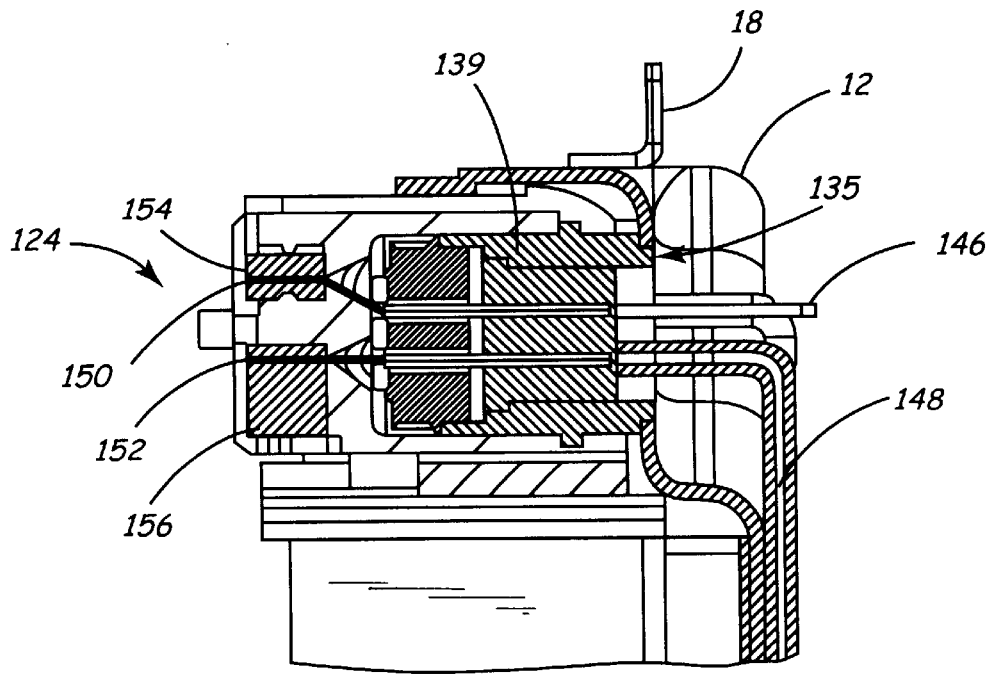
FIG. 30 is cross-sectional side view of one portion of a feedthrough assembly.

FIG. 28 is a cross-sectional view of a pair of feedthrough assemblies 24, 26 for incorporation in device 10. FIG. 29 is another cross-sectional view of feedthrough assemblies 24, 26 in conjunction with a portion of shield 12. FIG. 30 is a cross-sectional side view of one portion of feedthrough assembly 24. Feedthrough assemblies 24, 26 are positioned side-by-side within shield 12.

As shown in FIGS. 28–30, feedthrough assembly 24 includes a feedthrough terminal block 134 and a feedthrough 135, which can be bonded together with epoxy. Similarly, feedthrough assembly 26 includes a feedthrough terminal block 136 and a feedthrough 137. Feedthrough 137 includes a ferrule that holds a number of pins that are provided as termination points for diagnostic or therapeutic leads that extend from device 10. Feedthrough terminal block 136 contains a number of internal terminal contacts that provide termination points for the pins. Importantly, feedthrough assembly 26 must permit communication of the pins to the interior of device 10 but also hermetically seal the device from the implanted environment.

Feedthroughs 135, 137 are mounted within recesses defined by feedthrough terminal blocks 134, 136, respectively, and receive sets of conductive pins 28, 30. Each feedthrough 135, 137 may receive, for example, four pins 28, 30, with each feedthrough providing a quadripolar feedthrough. In some embodiments, less than all eight pins provided in feedthroughs 135, 137 may be used. In addition, feedthrough assemblies 24, 26 may be designed to hold different numbers of pins, depending on the application. Pins 28, 30 can be formed, for example, from electrically conductive materials such as tantalum. Sections 138, 140 encompass pins 28, 30 and are formed from a glass or ceramic material that encompasses the pins, and hermetically seals feedthrough assemblies 24, 26 from the implanted environment outside device 10.

Outer walls 139, 141 of feedthroughs 135, 137 enclose sections 138, 140, respectively. Sections 138, 142 and 140, 144 encompass conductive pins 28, 30, respectively, and form capacitive filters that reduce the effects of electromagnetic interference on the signals carried by the pins. Sections 142 and 144 are partially enclosed by outer walls 139, 141, respectively. With reference to FIG. 30, in particular, individual pins 146, 148 associated with one of feedthrough assemblies 24, 26 make contact with electrical contact elements 152, 154, respectively, within feedthrough terminal blocks 134, 136. Contact elements 152, 154 can be electrically coupled to circuit assembly 44 via parallel gap or ribbon bond welding. The structure of feedthroughs 135, 137 will be discussed in greater detail below.

Figure 31:
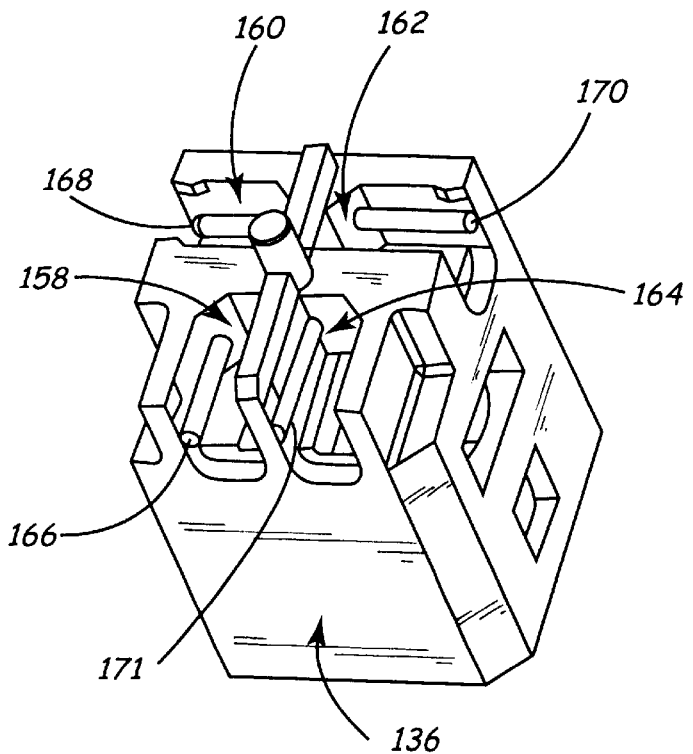
FIG. 31 is a perspective view of a terminal block associated with a feedthrough assembly.
Figure 32:
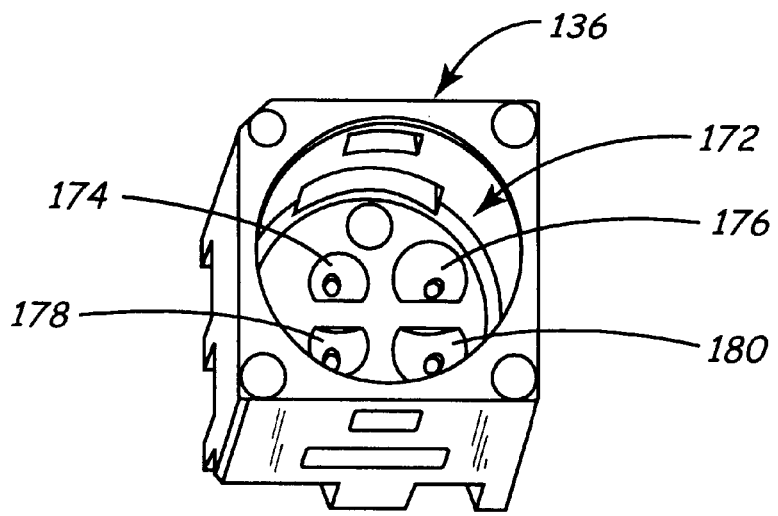
FIG. 32 is another perspective view of the terminal block of FIG. 31.

FIGS. 31 and 32 are different perspective views of a feedthrough terminal block 136. As shown, feedthrough terminal block 136 includes a number of terminal recesses 158, 160, 162, 164. Each terminal recess 158, 160, 162, 164 includes a set of mounting rails on opposite side walls of the respective recess. Mounting rails 166, 168, 170 are visible in recesses 158, 160, 162, for example, whereas an opposite mounting rail 171 is visible in recess 164. As further shown in FIG. 32, feedthrough terminal block 136 defines a circular aperture 172 facing outward toward an exterior side of the terminal block for receipt of a feedthrough 137. Within aperture 172, feedthrough terminal block 136 defines four channels 174, 176, 178, 180 for communication of pins 30 to terminal recesses 158, 160, 162, 164.

Figure 33:
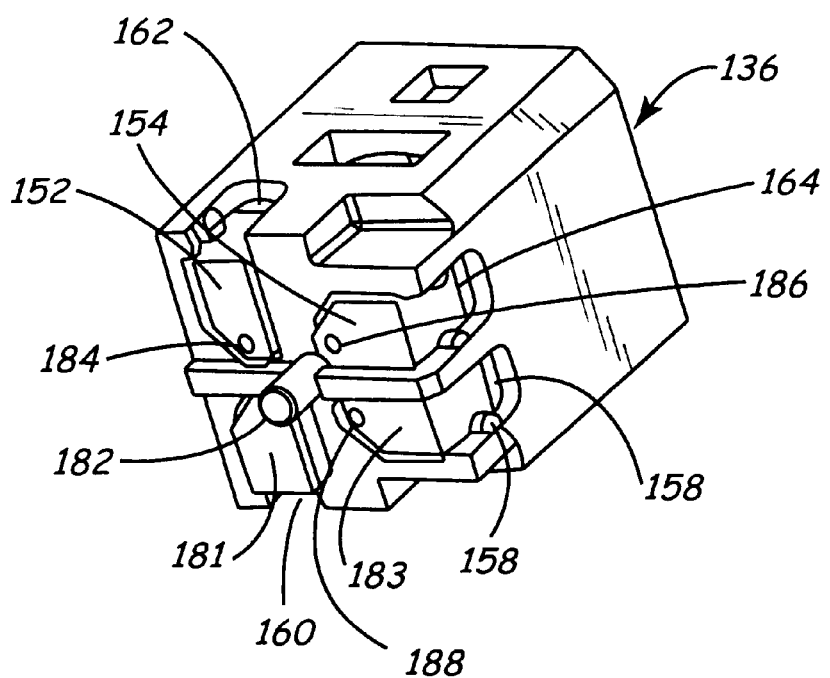
FIG. 33 is a perspective view of the terminal block of FIG. 31 illustrating incorporation of terminal contact elements.
Figure 34:
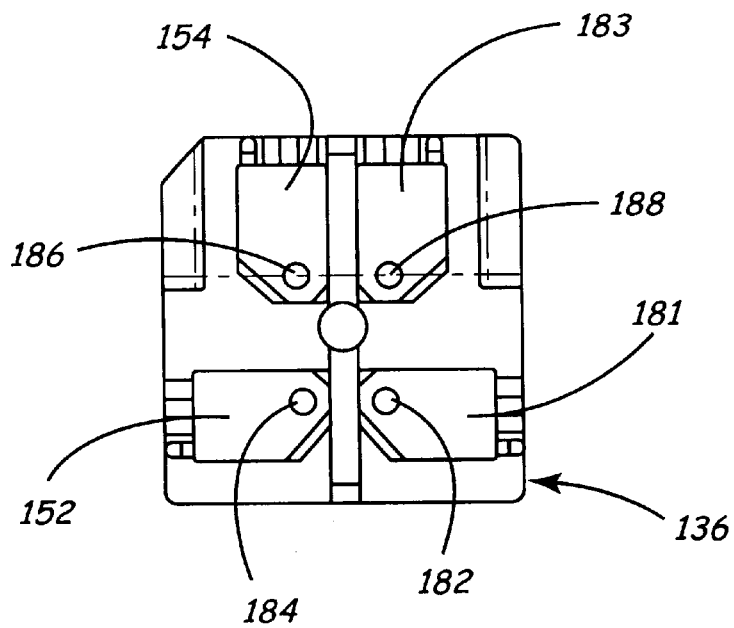
FIG. 34 is an end view of the feedthrough terminal block of FIG. 31.

FIG. 33 is a perspective view and FIG. 34 is an end view of the feedthrough terminal block of FIG. 31 illustrating incorporation of terminal contact elements 181, 152, 154, 183 within terminal recesses 158, 160, 162, 164 in an interior side of the feedthrough terminal block. Terminal contact elements 181, 152, 154, 183 can be mounted into the respective recesses 158, 160, 162, 164 along the mounting rails and press- or snap-fit into place. Contact elements 181, 152, 154, 183 may be formed, for example, from nickel. In some embodiments, recesses 158, 160, 162, 164 may be formed to provide snap-fit structures, which can be molded features of feedthrough terminal block 136. As an example, feedthrough terminal block 136 can be formed from a molded plastic material such as ULTEM™ plastic, available from General Electric Company. Thus, terminal block 136 serves as an insulative frame for contact elements 181, 152, 154, 183, and defines a platform for automated welding techniques to coupled the contact elements to respective terminals on flex circuit 50.

Figure 35:
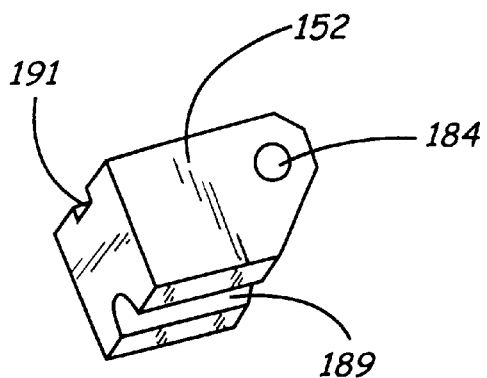
FIG. 35 is a first perspective view of a contact element for incorporation in the terminal block of FIG. 31.
Figure 36:
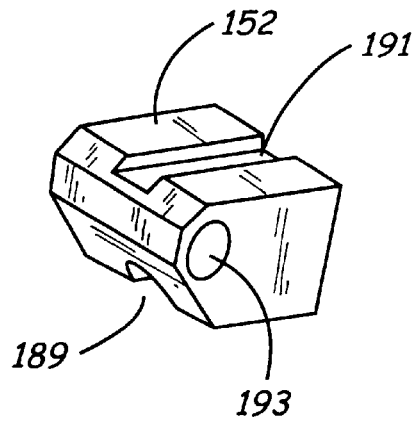
FIG. 36 is a second perspective view of the contact element of FIG. 35.

As further illustrated in FIGS. 33 and 34, each terminal contact element 181, 152, 154, 183 defines a pin channel with a first opening, 182, 184, 186, 188, respectively. FIGS. 35 and 36 are perspective views of a contact element 152 for incorporation in terminal block 136 of FIG. 31. FIG. 35 further illustrates first opening 184 of the pin channel formed in contact element 152, as well as mounting channels 189, 191, which mate with the mounting rails provided within recess 162. FIG. 36 illustrates a second opening 193 at an end of the pin channel opposite opening 182. Second opening 193 may have a diameter that is somewhat larger than that of first opening 184 to facilitate the threading of a pin through the pin channel. In particular, a pin introduced by a feedthrough will be introduced at opening 193 and threaded through the pin channel to terminate at opening 184, where the pin may be welded in place, i.e., welded to contact element 181.

Figure 37:
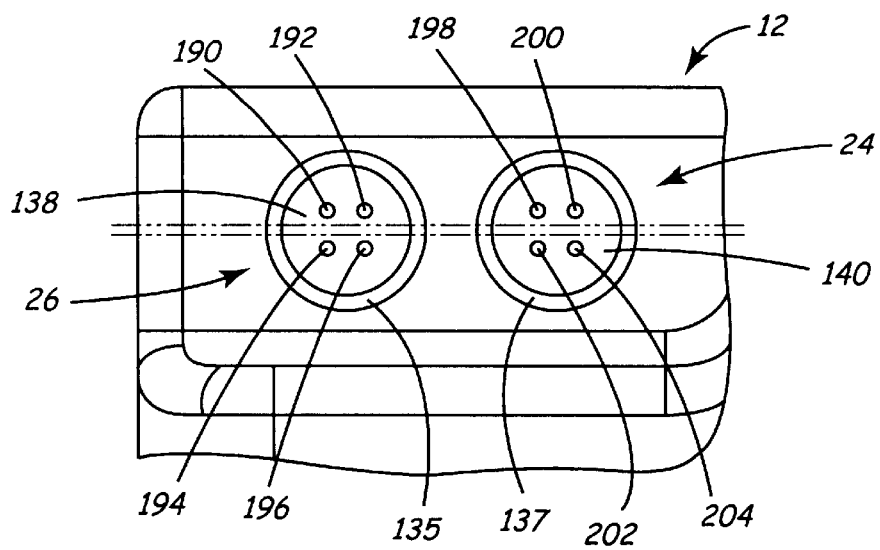
FIG. 37 is an end view of feedthroughs associated with the feedthrough assembly.
Figure 38:
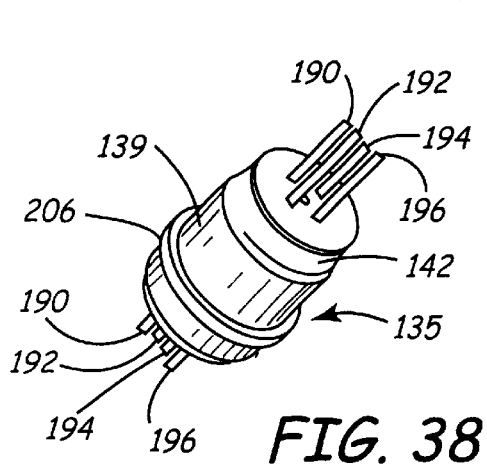
FIG. 38 is a first perspective view of a feedthrough associated with the feedthrough assembly.
Figure 39:
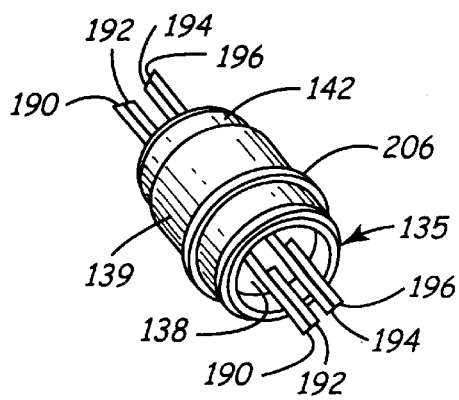
FIG. 39 is a second perspective view of a feedthrough.

FIG. 37 is an end view of feedthroughs 135, 137 associated with feedthrough assemblies 24, 26, respectively, from the exterior of device 10. FIGS. 38 and 39 are first and second perspective views of feedthrough 135. As shown in FIG. 37, feedthrough 135 receives a group of pins 190 192, 194, 196, and feedthrough 137 receives a group of pins 198, 200, 202, 204. FIGS. 38 and 39 show feedthrough 135, which includes an outer ferrule wall 139 into which seal section 138 and capacitor section 142 are inserted. Outer wall 139 defines a ridge 206 that abuts with feedthrough terminal block 136 upon placement of feedthrough 139 within recess 172 (FIG. 32) to limit the depth of insertion.

Figure 40:
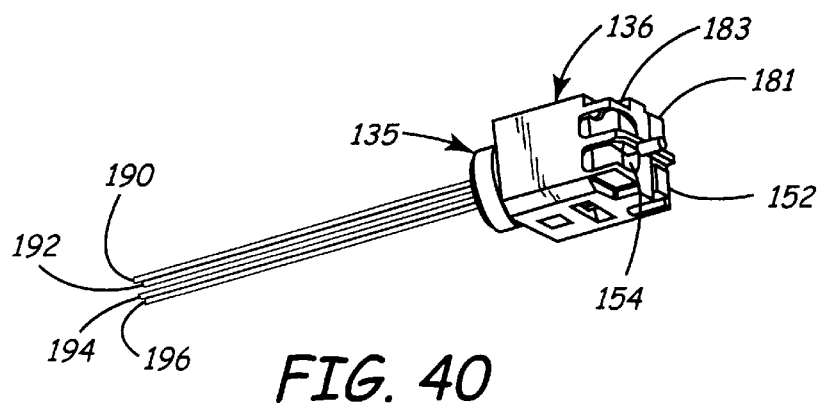
FIG. 40 is a perspective view of a feedthrough assembly incorporating a terminal block and a feedthrough.
Figure 41:
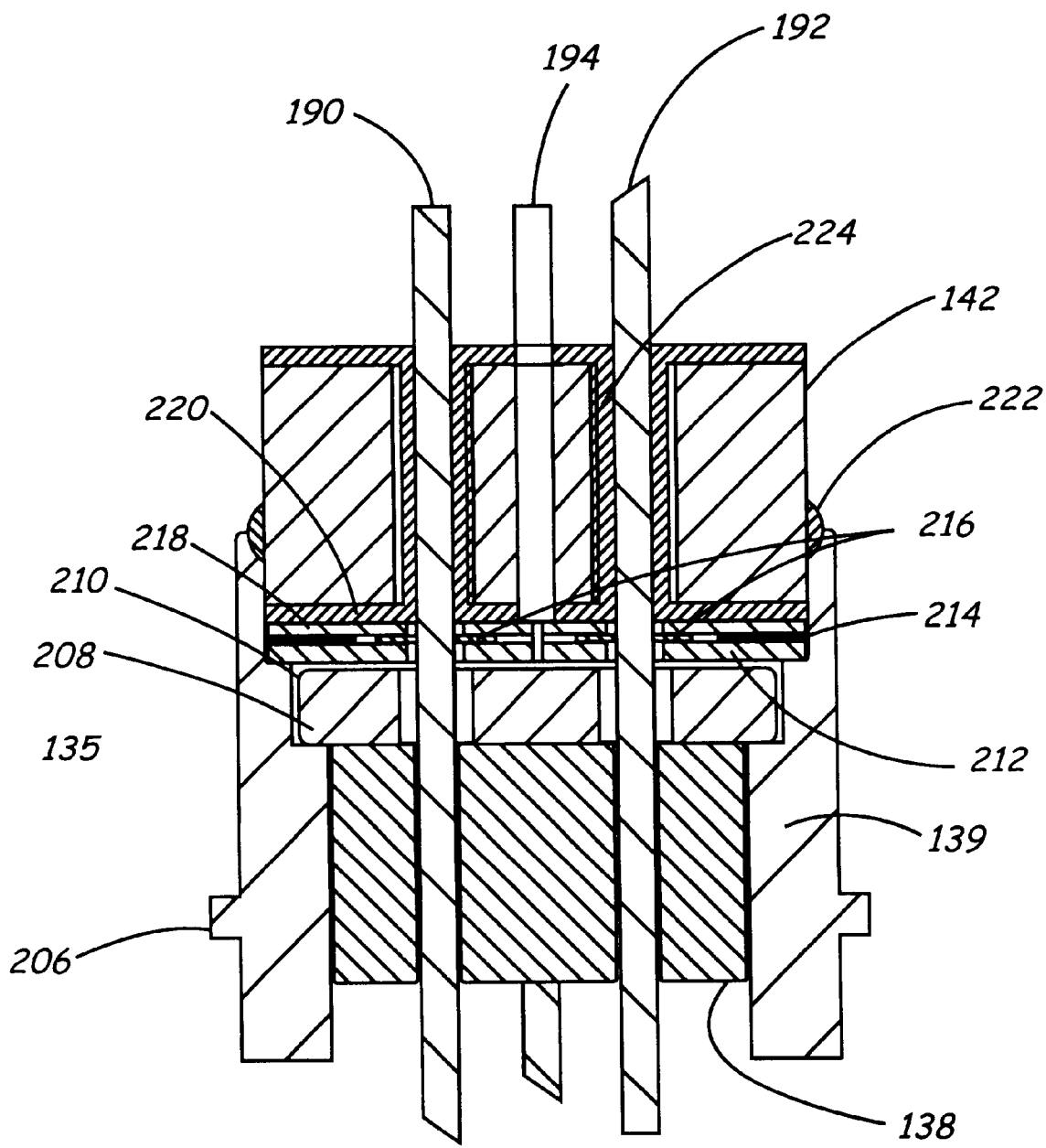
FIG. 41 is an enlarged cross-sectional side view of a feedthrough.

FIG. 40 is a perspective view of feedthrough assembly 24 with a feedthrough terminal block 136 and a feedthrough 135. FIG. 41 is an enlarged cross-sectional side view of feedthrough 135. FIG. 41 shows seal section 138 and capacitor section 142, as well as pins 190, 192, 194 which extend through feedthrough 135 to connect contact elements in feedthrough block 136 to external leads. Capacitor section 142 takes the form of a discoidal capacitor element that fills in the annular spaces between pins 190, 192, 194, 196 and filters electromagnetic interference. Pin 196 is not shown in FIG. 40. The capacitance between a pin and ferrule wall 139 may be on the order of 1000 to 2000 picofarads. Pins 190, 192, 194 can be welded to corresponding contact elements using automated welding techniques, simplifying attachment and promoting strength and reliability. Outer wall 139 can be made from a titanium alloy, and welded to shields 12, 14.

A layer 210 of non-conductive epoxy bonds a barrier glass 208 to the inner surface of ferrule wall 139 adjacent capacitor section 142. A metal platform washer 212, polyimide ferrule washer 214, and polyimide pin washer 216, and a polyimide platform washer 218 may be placed between barrier glass 210 and capacitor section 142. A nonconductive epoxy 220 bonds capacitor section 142 to glass 208 and washer 218. A circumferential layer 222 of conductive polyimide is applied between capacitor element 142 and ferrule wall 139. A layer 224 of conductive polyimide also lines the inner diameter of capacitor section 142 between pins 190, 192, 194. Pin 196 is not visible in the cross-sectional view of FIG. 41.

Various modifications to the apparatus or methods may be made without departing from the scope of the invention. These and other embodiments are within the scope of the following claims.

What is claimed is:

1. An implantable medical device comprising:

a housing;

a battery within the housing and having battery terminals;

a capacitor within the housing and having capacitor terminals; and a circuit assembly within the housing and having circuit terminals, wherein the battery terminals and the capacitor terminals form a first row of terminals, the circuit terminals form a second row of terminals adjacent the first row of terminals, and the circuit terminals are electrically coupled to the battery terminals and the capacitor terminals, wherein the first and second rows of terminals are substantially linear and extend substantially parallel to one another, and the circuit terminals are electrically coupled to the battery terminals and the capacitor terminals via parallel gap welded bonds or ribbon welded bonds.

2. The device of claim 1, wherein the battery is positioned side-by-side with a lower portion of the capacitor, and the circuit assembly is positioned over the battery and side-by-side with an upper portion of the capacitor, the battery and circuit assembly having a combined thickness that approximates a thickness of the capacitor.

3. The device of claim 2, wherein the circuit assembly and the capacitor present a generally planar surface, the device further comprising an interconnect assembly mounted over the generally planar surface and interconnecting the capacitor terminals and the circuit terminals.

4. The device of claim 3, wherein the first and second rows of terminals are substantially linear and extend substantially parallel to one another, the interconnect assembly includes conductive ribbons oriented to bridge adjacent terminals in the first and second rows of terminals, and the circuit terminals are electrically coupled to the battery terminals and the capacitor terminals via welded bonds formed by the conductive ribbons.

5. The device of claim 1, wherein the capacitor includes a terminal block assembly that extends outward from the capacitor and positions the capacitor terminals adjacent the battery terminals along a lateral surface of the battery.

6. The device of claim 1, wherein the first row of terminals is positioned along a lateral surface of the battery, and the second row of terminals is positioned along an edge of the circuit assembly.

7. The device of claim 1, further comprising an interconnect assembly positioned within the housing, wherein the interconnect assembly includes a first set of interconnect terminals positioned adjacent and electrically coupled to at least some of the circuit terminals, a second set of interconnect terminals positioned remotely from the circuit terminals, and conductors that electrically couple the first and second sets of interconnect terminals.

8. The device of claim 7, wherein the interconnect terminals include conductive ribbons oriented to contact at the least some of the circuit terminals.

9. The device of claim 8, wherein the first set of interconnect terminals form a third row of terminals substantially parallel to the first and second rows of terminals, the first set of interconnect terminals being electrically coupled to the at least some of the circuit terminals via parallel gap welded bonds or ribbon welded bonds.

10. The device of claim 9, wherein the interconnect assembly includes an antenna for radio frequency telemetry and an audible alarm device electrically coupled to the at least some of the circuit terminals via the first set of interconnect terminals.

11. The device of claim 8, wherein the battery and the capacitor are positioned side-by-side, the circuit assembly is positioned over the battery, and the interconnect assembly is positioned over the circuit assembly and the capacitor.

12. The device of claim 7, further comprising a feedthrough assembly positioned within the housing and having feedthrough terminals positioned adjacent and electrically coupled to one or more additional terminals that electrically couple at least some of the feedthrough terminals to at least some of the circuit terminals.

13. The device of claim 12, further comprising a flex circuit connector that electrically couples the feedthrough terminals to the at least some of the circuit terminals.

14. The device of claim 12, further comprising one or more pins that extend from the feedthrough assembly and outward from the housing, wherein the circuit assembly includes a charging circuit that applies current from the battery to charge the capacitor, and a pulse generation circuit that applies current from the capacitor to deliver electrical pulses to the pins via the feedthrough terminals for cardiac stimulation.

15. The device of claim 14, wherein the feedthrough assembly includes an electrically insulative terminal block, multiple contact elements mounted in an interior side of the insulative terminal block to form the feedthrough terminals, and first channels formed in an exterior side of the insulative terminal block for communication of the conductive pins to the contact elements.

16. The device of claim 15, wherein the contact elements define second channels in communication with the first channels, the pins being threaded through the first and second channels and fixed in place to electrically couple the pins to the contact elements.

17. The device of claim 16, wherein proximal ends of the pins are welded to the contact elements.

18. The device of claim 15, wherein the feedthrough assembly includes first and second feedthrough assemblies, each of the first and second feedthrough assemblies accommodating at least two of the conductive pins.

* * * * *